United States Patent [19]
Chess

[11] Patent Number: 5,486,172
[45] Date of Patent: Jan. 23, 1996

[54] APPARATUS FOR TREATING CUTANEOUS VASCULAR LESIONS

[76] Inventor: Cyrus Chess, 49 Blue Spruce Cir., Weston, Conn. 06883

[21] Appl. No.: 189,942

[22] Filed: Jan. 31, 1994

Related U.S. Application Data

[63] Continuation-in-part of Ser. No. 706,243, May 28, 1991, Pat. No. 5,282,797, which is a continuation of Ser. No. 358,890, May 30, 1989, Pat. No. 5,057,104.

[51] Int. Cl.$^6$ .................................................. A61N 5/06
[52] U.S. Cl. .................................. 606/20; 606/2; 606/9; 606/10; 607/96; 607/99; 607/112; 607/114; 206/45.34; 206/524.4; 220/4.21; 220/501; 220/529; 220/602; 220/665; 62/259.3; 62/529
[58] Field of Search ............................... 607/96, 104, 99, 607/108–112, 114; 606/20, 27, 28, 31, 2, 9–11; 220/501, 529, 602, 662–665, 4.21; 206/15.1, 45.31, 45.34, 524.4; 62/529, 530, 259.3

[56] References Cited

U.S. PATENT DOCUMENTS

| | | | |
|---|---|---|---|
| 2,702,552 | 2/1955 | Moodie | 607/108 |
| 2,715,315 | 8/1955 | Giardini | 607/112 |
| 3,854,153 | 12/1974 | Williams | 607/96 |
| 4,071,031 | 1/1978 | Lowman | 607/108 |
| 4,149,529 | 4/1979 | Copeland et al. | 607/104 |
| 4,329,997 | 5/1982 | de Yampert et al. | 607/114 |
| 4,516,564 | 5/1985 | Koiso et al. | 67/114 |
| 4,761,047 | 8/1988 | Mori | 607/96 |
| 5,190,032 | 3/1993 | Zacoi | 607/104 |

Primary Examiner—David M. Shay
Attorney, Agent, or Firm—Ohlandt, Greeley, Ruggiero & Perle

[57] ABSTRACT

An apparatus is provided for treating cutaneous vascular lesions in a target area of a patient. The apparatus has a lower housing having a bottom with an opening therethrough, and an upper housing adapted to be connected in liquid tight engagement to the lower housing. The upper housing has a top with an opening therethrough and substantially in alignment with the opening of the lower housing. A pair of glass windows are provided one positioned in the opening of the lower housing, and the other positioned in the opening of the upper housing. The apparatus further comprises at least one fenestrated wall adapted to be removably positioned in the lower housing to form a first and a second chamber when the upper and lower housings are connected together. The first chamber is adapted to receive a cooling medium, and the second chamber prevents the cooling medium from obstructing the passage of a laser beam between the pair of glass windows. The fenestrated wall provides for the passing of any portion of the cooling medium in liquid form to move through the apparatus.

21 Claims, 4 Drawing Sheets

APPARATUS FOR TREATING CUTANEOUS VASCULAR LESIONS

RELATED APPLICATIONS

This application is a continuation-in-part of application Ser. No. 07/706,243, filed May 28, 1991, now U.S. Pat. No. 5,282,797, which in turn is a continuation of application Ser. No. 07/358,890, filed May 30, 1989, now U.S. Pat. No. 5,057,104, which issued on Oct. 15, 1991.

BACKGROUND OF THE INVENTION

I. Field of the Invention

The present invention relates generally to an apparatus for treating cutaneous vascular lesions and, more particularly, to such an apparatus that readily attaches to the patient. This apparatus in conjunction with the apparatus disclosed in the above applications provide for the treatment of cutaneous vascular lesions by simultaneously cooling the site of the lesions while delivering laser light to the site.

II. Description of the Prior Art

A cutaneous vascular lesion, such as telangiectasia or spider capillaries of the lower extremities, is a condition where previously microscopic blood vessels have become dilated. They are visible through the skin appearing as red, blue or purple variably tortuous lines or patches. The causes of this abnormal enlargement of vessels are not fully understood, and although they are of little medical consequence their cosmetic significance can be great. This is a widespread problem that may cause much concern for those afflicted.

Sclerotherapy is the treatment that is now used. It is considered to be safe, appropriate and relatively effective. Sclerotherapy entails the intravascular injection of one of a variety of agents into the abnormal blood vessels. The substance injected injures the inside of the capillary causing it to shrink or disappear. This treatment is variably painful, approximately seventy percent (70%) effective, and usually requires one to two months waiting before improvement can be seen. There can occur, unpredictably, echymotic or hyperpigmented marks as a side effect. These marks may take many months to fade. Scabbing of injection sites, perhaps due to extravasation of the injected sclerosing agent, may also occur.

The disadvantages of sclerotherapy, as described above, include the pain of treatment, only partial improvement, and the possibility of long term discoloration that can be more noticeable than telangiectasia.

Laser surgery with a variety of different lasers ($CO_2$, Argon, tunable dye, pulsed dye, KTP, Nd/YAG) has been utilized in an attempt to find a less painful, more effective treatment. The desire to avoid side effects has also prompted a search for alternative treatment. To date, the ability to improve the outcome by virtue of laser surgery has, unfortunately, not been possible for reasons explained below.

Although laser surgery (Argon or dye) hurts less than sclerotherapy, it has not offered an improved result. Due to the interaction between laser light and melanin pigments in the epidermis that overlies the target vessels, there can be long term hyperpigmentation, persistent scabs and sometimes permanent scarring.

More recently, medical specialists have attempted to minimize hyperpigmentation, scabs and scarring caused by laser surgery by cooling the lesional site for a given period of time before initiating any treatment by laser surgery. The results of such treatment have proven to be more satisfactory than sclerotherapy or laser surgery alone, as provided in the following two articles.

In *Plasti. Reconstr. Surg.* 6902:78 (1982) in an article titled "Chilling Port Wine Stains Improves The Response To Argon Laser Therapy" by B. A. Gilchrest, S. Rosen and J. M. Noe, the data obtained in this study suggests the potential benefit of port wine lesional modification by chilling the lesional site by applying ice thereto for 2 to 3 minutes and then subjecting the sites to Argon laser therapy. Ice cubes were applied to the skin surface by enclosing them in an examining glove.

In *Plasti. Reconstr. Surg.* 75.1:42–45 (1985) in an article titled "The Benefit of Chilling In Argon-Laser Treatment of Port-Wine Stains" by B. Dreno, T. Patrice, P. Litoux and H. Barriere, the authors compare results obtained in Argon laser treatment of port-wine stains with and without preliminary chilling, noting that the success rate is considerably greater with the former procedure (68.6 percent) then with the latter (37.5 percent). For this experiment, an ice bag was applied to port-wine stain for 5 minutes immediately before the beginning of treatment. During the treatment, the ice bag was applied again after 2 minutes of laser use.

It should be noted that in the studies noted in the above articles, Argon laser treatment and cooling did not occur simultaneously, and the Argon laser could not reach the port-wine stain while the examining glove or ice bag covered up the treatment area.

U.S. Pat. No. 3,821,510 to Muncheryan, which issued on Jun. 28, 1974, is directed to a hand-held laser beam transmitting and focusing stylus in which there is provided means for selectively passing therethrough one or more fluids simultaneously with the operation of the device. Since the cooling fluid is passed through a flexible tubing and an upper end of the stylus, the lower end of the stylus that touches the skin provides a small area where cooling may take place.

Although the stylus of Muncheryan provides a laser treatment device that cools a portion of a patient's skin, its cooling elements is confined to the area treated by the laser beam. Also, the cooling element readily dissipates, such that constant replacement is required in order to keep the area cooled. Further, the Muncheryan patent neither recognizes the benefits of cooling a broad area of a patient's skin for treatment, including the minimization of hyperpigmentation, scabs and scarring caused by laser surgery nor the need for a container to maintain the cooling element.

The Muncheryan patent, like all known references, fail to provide an apparatus that contains the cooling medium, yet provides for simultaneous cooling and lasering of a target. Moreover, the present apparatus provides the simultaneous cooling and laser application, but without any obstruction of the path of the laser beam through the apparatus.

The above related priority applications have provided improved methods of treatment by the use of a container to retain the cooling element and to permit the simultaneous cooling and treatment of the target area. However, the container disclosed in these applications failed to appreciate the features of the container of the present application.

Thus, the present invention provides a new laser surgery apparatus to allow for laser photo-coagulation and destruction of cutaneous vascular lesions, such as, for example, lower extremity telangiectasia, while protecting the epidermal compartment from thermal injury that would otherwise result from absorption of laser energy by melanin. Since laser light must pass through the melanin containing epidermis, on its way to the target vessels in the dermis, it is not possible to prevent some degree of heat generation when laser light hits melanin pigment. Indeed, yellow (tunable dye) laser light, although less efficiently absorbed by melanin than is blue-green (Argon) laser light, still causes significant hyperpigmentation as a long term side effect. Thus, cooling dissipates the heat generated by absorption of that light by melanin, thereby minimizing injury to normal skin structures to reduce resulting pain and side effects of scabbing scarring and/or hyperpigmentation. Significantly, the present apparatus permits the epidermis to be cooled simultaneously with the use of laser light, while maximizing the length of time before replacement of the cooling medium and thereby reducing the frequency of replacement of the cooling medium. In addition, the apparatus is constructed such as to minimize obstruction to the path followed by the laser beam.

Thus, the present invention discloses an efficient and economical apparatus for simultaneous cooling during laser treatment of cutaneous vascular lesions. The apparatus can be readily positioned on a large area of the epidermis to be treated, thereby, maximizing the cooling effect during the laser treatment. Further, the apparatus is separate and distinct from the laser beam source so as to utilize present, readily-available laser types without resorting to expensive and complicated devices that integrate laser beams with cooling devices.

Also, the present apparatus permits one to position the cooling medium where desired on the patient. In addition, it permits one to be free to position the laser beam in relation to the apparatus, thus providing needed flexibility.

SUMMARY OF THE INVENTION

Against the foregoing background, it is a primary object of the present invention to provide an apparatus for treating cutaneous vascular lesions.

It is another object of the present invention to provide such an apparatus that separates the travel path of the laser beam from the position of any solid cooling medium, yet permits the laser beam and the solid cooling medium to affect the target area simultaneously.

It is still another object of the present invention to provide such an apparatus that, if desired, provides separate compartments that provides a chamber for a liquid cooling medium and as a path for a laser beam, and a pair of compartments that contain a solid cooling medium thereby maintaining the temperature of the liquid cooling medium during laser treatment.

It is yet another object of the present invention to provide such an apparatus that includes at least one fenestrated internal wall that provides a compartment for solid cooling medium that is unaffected by the laser treatment. In the preferred embodiment, a second fenestrated internal wall is utilized to provide for more than one compartment for one or more solid cooling mediums, yet provides a separate compartment to prevent obstruction of the laser beam path and a chamber to hold a liquid cooling medium.

It is a further object of the present invention to provide such an apparatus that permits changing the size of the compartments, as well as the ready replacement of the cooling mediums and the desired ready removal of air.

To the accomplishment of the foregoing objects and advantages, the apparatus of the present invention, in brief summary, comprises a container for use in conjunction with a laser beam source to treat a target area, such as a epidermis. The container has an upper housing, a lower housing and means for securing together the upper and lower housings.

The upper housing and the lower housing each has a window area for permitting the laser beam therethrough. The container has at least one fenestrated wall that is adapted to be positioned in the container to form a first compartment and a second compartment inside the container, and means for securing the fenestrated wall into place in the container. The first compartment is adapted to contain a solid cooling medium, and a second compartment is adapted to contain a liquid cooling medium and also prevent the solid cooling medium from obstructing the passage of the laser beam.

The at least one fenestrated or perforated wall permits the liquid cooling medium to flow freely in the container so that cooling medium is placed on the target area. The container also has means for permitting the ingress of a fluid cooling medium or the egress of air and dissipated cooling medium, and means for securing the container into a desired position on a user's body.

In a preferred embodiment, the container has two fenestrated walls that separates the container into three compartments. Preferably, the second compartment is positioned between and adjacent both the first and the third compartments. The laser beam passes through that second or middle compartment and does not affect the solid cooling medium in the first and third compartments. The second compartment is filled with liquid cooling medium. Accordingly, the second compartment has liquid cooling medium at the point where the laser beam strikes the target area. However, the solid cooling medium is not in the path of the laser beam so that the cooling medium in these lateral compartments act to maintain the level and temperature of the liquid cooling medium in the second compartment.

When the container is used to treat cutaneous vascular lesions in a target area of the patient, the container should be liquid tight with the second or middle compartment entirely filled with a liquid cooling medium, such as cooled water, and the two lateral compartments filled with solid cooling medium, such as ice cubes. All air should be removed from the inside of the container by the means to permit the egress of air, as well as cooling medium, from the container.

The above, and other objects, features and advantages of the present invention will become apparent from the following description read in conjunction with the accompanying drawings, in which like reference numerals designate the same elements.

BRIEF DESCRIPTION OF THE DRAWINGS

The foregoing and still other objects and advantages of the present invention will be more apparent from the following detailed explanation of the preferred embodiments of the invention in connection with the accompanying drawings wherein.

DETAILED DESCRIPTION OF THE PREFERRED EMBODIMENT

Figure 1:
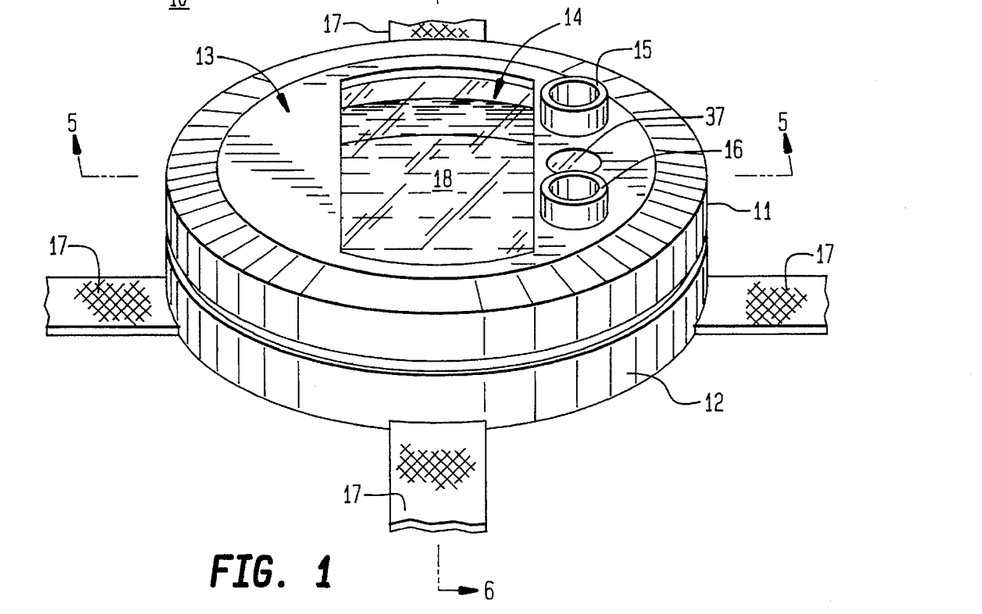
FIG. 1 is a perspective view a preferred embodiment of the apparatus of the present invention.

Referring to the figures and, in particular, FIG. 1, there is shown an apparatus or container having a housing generally represented by reference numeral 10.

The housing 10, preferably, is in the shape of a flat, yet thick, disc. The housing 10 basically comprises an upper housing 11 and a lower housing 12. The upper housing 11 and lower housing 12 are adapted to be secured together in liquid tight engagement. In a preferred embodiment, they are secured together by screwing threads located on each housing.

Specifically, either the upper housing 11 or the lower housing 12 has a male thread while the other housing has a complementary female thread. Preferably, a sealing element (not shown) made of a flexible, water tight material, such as silicone, may be interposed between the upper housing 11 and the lower housing 12 to maintain a fluid tight seal when the upper housing and lower housing are connected together. In the preferred embodiment shown in FIGS. 2 and 7, the upper housing 11, has threads molded on an inner portion of outer lip 21, and the lower housing 12 has mating threads molded on the outer portion of its inner lip 22. As upper housing 11 is turned in a clockwise direction on the top of the lower housing 12, the threads of outer lip 21 and the inner lip 22 shall join together, forming a tight seal between the housings. Turning the upper housing 11 in a counterclockwise direction will remove the upper housing from the lower housing 12. To facilitate removal, the lower housing 12 has an inner lip base 23 that extends radially out further than the inner lip 22, giving a user a more accessible portion of the lower housing to grip.

The lower housing 12 has an outside bottom surface that is flat, however it may be contoured to better fit the contour of the patient's body. The upper housing 11 has three openings 15, 16 and 37 that are positioned through the top surface of the upper housing.

The upper housing 11 and the lower housing 12 are made of a material well suited for contact with human skin, such as a polyphenylene oxide (CAS #25134-10-4)/high impact polystrene (CAS#9003-55-8) polymer blend. The preferred polymer blend is sold under the trademark NORYL, as NORYL resin 731-873S. It is made by General Electric Company and sold by GE Plastics Canada, Ltd. This material has been selected since it is easy to work with and is in full compliance with FDA safety regulations regarding substances that come in contact with skin. It is also sturdy and relatively light in weight. In addition, the autoignition is estimated to be 490 degrees Centigrade (914 degrees Fahrenheit), and requires a continuous flame to ignite. Also, this material is not sensitive to mechanical impact and is not sensitive to static discharge.

It is believe that rigid Nylon may be used as an alternative material. However, it is not certain whether rigid Nylon is in full compliance with FDA safety regulations, and may be more difficult to work with.

Figure 2:
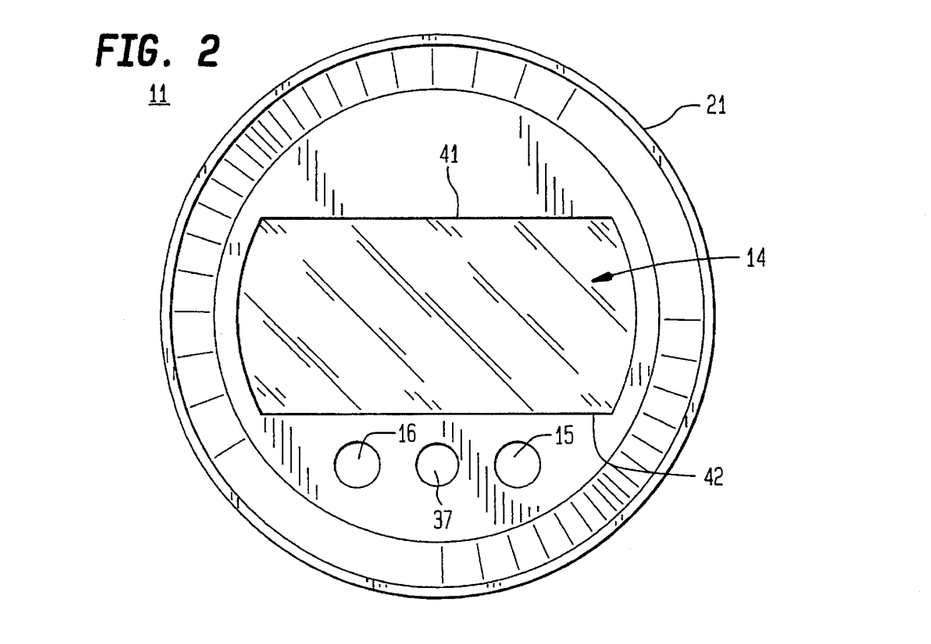
FIG. 2 is a planar view of the inside surface of the upper housing of FIG. 1.
Figure 3:
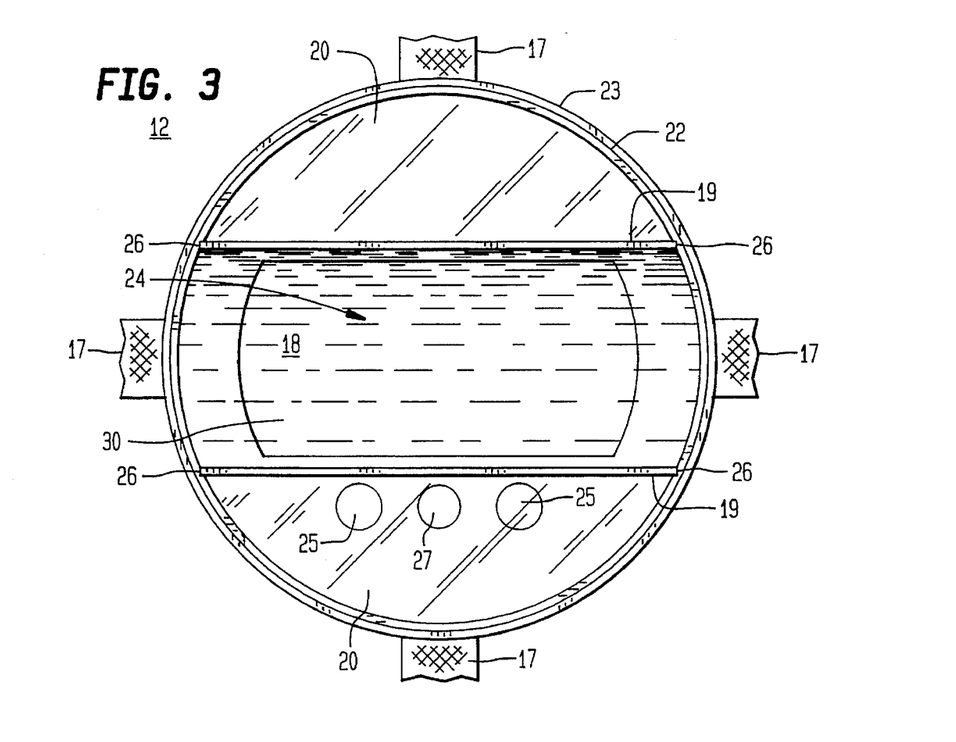
FIG. 3 is a planar view of the inside surface of the lower housing of FIG. 1.

Referring to FIGS. 2 and 3, the upper housing 11 and the lower housing 12 each has a centered opening that permits the insertion of a glass window 14 and 30, respectively. The glass window 14 is, preferably, flush mounted into the inside surface of the upper housing 11, and the glass window 30 is, preferably, flush mounted into the inside surface of the lower housing 12. Preferably, each glass window 14, 30 is about 0.175 inches or 3,175 millimeters in thickness and made of a quartz glass for optimal transmission of laser energy since such glass is clear and optically correct. A regular window glass may be used, however such glass would reduce the transmission by approximately 10%.

In a preferred embodiment, a non-reflecting coating is treated on the surface of each glass window 14, 30, to avoid reflection that would otherwise interfere with the laser beam and, thus, any surgical procedure.

When the housing 10 is positioned for use on the epidermis of a patient, the glass window 30 located at the underside of the lower housing 12 touches the patient. Like the glass window 14, the glass window 30 is, preferably, flush mounted into the surface of the shell and is made of a material that is unobstructive to laser light and, preferably, is substantially transparent. The surgeon may view the patient's epidermis through the glass windows 14 and 30. Significantly, the laser beam used for treating the patient's target area travels through the glass windows 14 and 30. By the construction of the present container, only a fluid cooling medium 18 has any affect on the path of the laser beam through the container and, thus, offers minimum, if any, obstruction to the laser beam.

Figure 5:
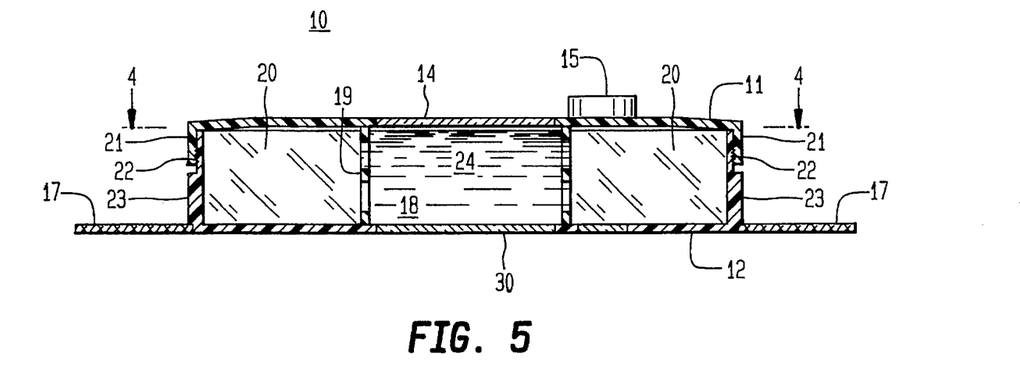
FIG. 5 is a cross-sectional view, taken along line 5—5, of FIG. 1.

As shown in FIG. 2, the outer lip 21 has treads molded on its inner portion. Two opposite sides of glass window 14 are shaped to conform with the curved, outer boundary of upper housing 11 in order to maximize coverage in that direction. The other two opposite sides 41, 42 of glass window 14 are, preferably, substantially parallel. These sides 41, 42 align with the placement of the fenestrated walls 19, as shown in FIG. 5. As shown in FIG. 3, two opposed sides of the glass window 30 conform with the outer boundary of the lower housing 12 and the other two opposed sides, that are preferably parallel, align with the placement of the fenestrated walls 19. The inner lip base 23 of the lower housing 12 has the molded threads on its outer portion, and has an outer diameter slightly smaller that the diameter of the inner lip 22 to permit engagement to the outer lip 21 of upper housing 11.

Referring again to FIG. 1, a logo area 13 is provided on the outside surface of the upper housing 11. Preferably, it is positioned on one side of the glass window 14, while the openings 15, 16 and 37 are positioned on the other side. The logo area 13 provides for a clear and unobstructive position of information regarding the identification or use of the present invention. For example, a logo of the manufacturer or warning labels may be easily seen by a user if placed at the logo area 13 of the upper housing 11.

The opening 15 is preferably an inlet opening that provides an entrance port into the housing 10 for a fluid cooling medium 18, such as, for example, water. The cooling medium 18 may flow freely throughout the inside of housing 10 and can exit the housing through the second or outlet opening 16. In one preferred embodiment, a cooling means, such as an external rechiller, re-cools the cooling medium exiting outlet opening 16 and recirculates the cooling medium back through inlet opening 15.

The outlet opening 16 also provides for the removal of air from inside the housing 10. In the surgical procedure in which the subject container is used, there should be no air in the housing and the container should, preferably, be entirely filled with cooling medium. Accordingly, should some air be present in the container, one would simply open the inlet opening 15 and the outlet opening 16 and permit fluid to enter the inlet opening and all of the air in the container to emit through the outlet opening out of the container.

The third opening 37 is for viewing purposes. This third opening 37 can be covered by a transparent medium, such as glass, so that nothing will enter into the container and no fluid will emit from the container, yet viewing of the inside of the container and through and to the other side of the container is easily effected.

Although only three openings are shown in FIG. 1, two or four or more openings may be implemented so long as the path traveled by the treating laser beam is not significantly obstructed.

In a preferred embodiment, the inlet opening 15 and the outlet opening 16 have hollow projections that project above the top surface of the upper housing 11. Accordingly, the hollow projection structure permits ready attachment of tubes, such as tubes 27 and 28 shown in FIG. 6, and valves to control the ingress of cooling medium 18 and the egress of air and the cooling medium from the housing 10. Also, by this construction, the projections of openings 15 and 16 permit a cap to be placed thereon. Therefore, should there is no desire to transport liquid cooling medium or air into the container, a cap can be placed on the projection of opening 15. Also, should the operator desire to prevent removal of dissipated or any fluid cooling medium from the container, a cap can be placed on outlet opening 16. Thus, this hollow projection structure permits for the interchangeable use of the housing with a solid cooling medium or a liquid cooling medium or both types of cooling mediums, and also provides for the controlled ingress and egress of cooling medium in liquid form and air.

Figure 6:
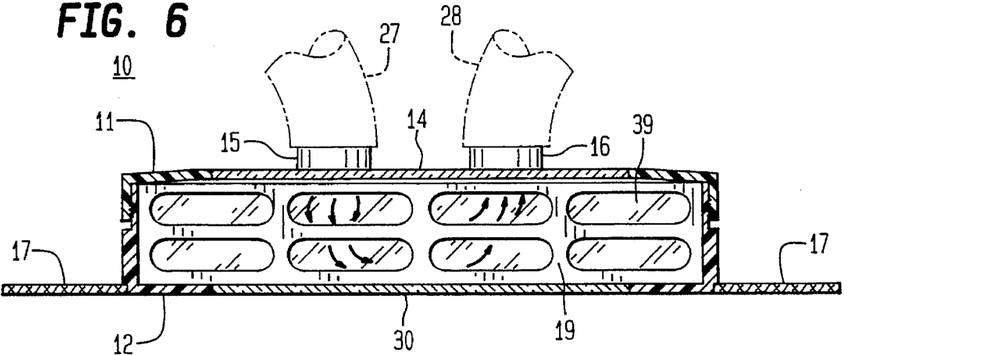
FIG. 6 is a cross-sectional view, taken along line 6—6, of FIG. 1.

Also, as shown in FIG. 6, the inlet tube 27 and the outlet tube 28, can provide a source and a collector, respectively, for the cooling medium 18 at the lateral chamber behind the wall 19. For example, the other ends of the inlet tube 27 and the outlet tube 28 can be connected to an external and separate chiller (not shown) for the cooling medium. Also, the cooling medium is circulated through the housing 10 as the inlet tube 27 on the projection of inlet opening 15 supplies new or recooled water and the outlet tube 28 on the projection of the outlet opening 16 removes dissipated, cooled water. This recirculation of cooling medium can be employed either alone or in conjunction with the use of a solid cooling medium, such as ice.

Referring to FIG. 5, the housing 10 is divided into separate chambers or compartments by one or more interior walls 19. In the preferred embodiment shown, a pair of walls 19 are used and these walls are spaced apart and, preferably, parallel to each other. The walls 19 are removable, thereby, providing for multiple configurations and quantities of chambers. In a preferred embodiment, each wall 19 is sized so that it contacts the inside surface of the upper housing 11, as well as the inside surface of the lower housing 12, when the upper housing and lower housing are secured together.

As shown more clearly in FIG. 6, a plurality of openings 39 exist in each fenestrated wall 19. The fenestrated, i.e. perforated, walls 19 allow the cooling medium 18 to flow freely therethrough, thereby minimizing the restriction of movement by the cooling medium. Yet, each wall 19 prevents the solid cooling medium, such as, for example, ice, from moving from compartment to compartment.

Each fenestrated wall 19 is designed to have the greatest amount of open area to permit unobstructed flow of the cooling medium, while preventing solids, such as pieces of ice, from interfering with the laser beam traveling through middle compartment 24. Accordingly, the size of each hole or opening 39 in each wall 19 should be as large as permitted to maximize the opening and, thereby, minimize the barrier portion of the wall. In the preferred embodiment shown in the FIGS., there are two rows of holes 39 in each wall. Each row has four holes. Each hole 39 has, in the preferred embodiment shown, an elongated oval shape and is about twenty-seven (27) millimeters (mm) wide by about six (6) mm high.

It is contemplated that any quantity or variety shapes of holes 39 of the fenestrated wall 19 may be used so long as ice movement into the middle compartment 24 is avoided.

In the preferred embodiment shown clearly in FIG. 5, two fenestrated walls 19 are used so that there is formed a middle compartment 24 and two lateral compartments 20. This embodiment is preferred because the middle compartment 24 provides the laser beam with a large central area to pass through. Also, the middle compartment 24 is entirely filled with the liquid cooling medium 18, while each lateral compartment 20 contains solid cooling medium that maintains the fluid cooling medium at an appropriate temperature. Obviously, if the solid cooling medium was contacted by the laser beam, the laser beam would cause a quicker warming (dissipation) or melting of the cooling medium in the container.

In addition, each lateral compartment 20 may contain cooling medium, such as, for example, a formed ice cube, preferably, of the same size and/or shape as the lateral compartment. In the preferred embodiment, the shape of the ice cubes 29 should be a half moon shape as shown clearly in FIG. 7. The formed ice cubes may be produced from plastic molds, that are accessories to the apparatus of the preferred embodiment, forming ice of appropriate size and shape.

The inlet opening 15 is located in the top wall of the upper housing 11 above one of the lateral compartments 20, and not above middle compartment 24. Thus, the inlet opening 15 is situated such that cooling medium will be directed only into a lateral compartment 20, and not in the middle compartment 24. The purpose of such a construction is to prevent new liquid cooling medium from entering into the middle compartment 24, and thus avoid disturbing the laser beam. Similarly, the outlet opening 16, shown in FIG. 1, which controls the outflow direction of the cooling medium so as to limit current flow within the middle compartment 24 to also avoid disturbing the path of the laser beam.

The preferred embodiment has two fenestrated internal walls 19 that are adapted to be positioned in the housing 10 in substantially parallel alignment with respect to each other. The walls 19 are secured within housing 12 by slidably mounting them into position on support notches 26 located on the inner periphery of inner lip 22 and inner lip base 23. Although any number of support notches have been contemplated for the housing, two support notches are necessary for each wall 19. The support notches 26 allow for the walls 19 to slidably fit securely within the lower housing 12 and yet remain easily removable. Thus, a user can easily configure the lower housing 12 to utilize two walls 19, or just one wall, or no walls, as the user desires.

The inside surface of the lower housing 12, preferably, has a pair of rings 25 that align with openings 15 and 16. These rings can serve to maintain a tube that may be placed entirely through the openings 15 and 16. A third ring 27 aligns with the opening 37, and is also transparent to permit viewing of the inside of the container and the other side of the container. Also, for manufacturing purposes, each ring 25 can contain a piece of material that can be readily removed so that each ring 25 can become an opening that, preferably, would be covered by glass or another transparent medium. By this structure, the manufacturing can be uniform so that a housing half can be made interchangeably into an upper housing 11 or a lower housing 12.

Figure 4:
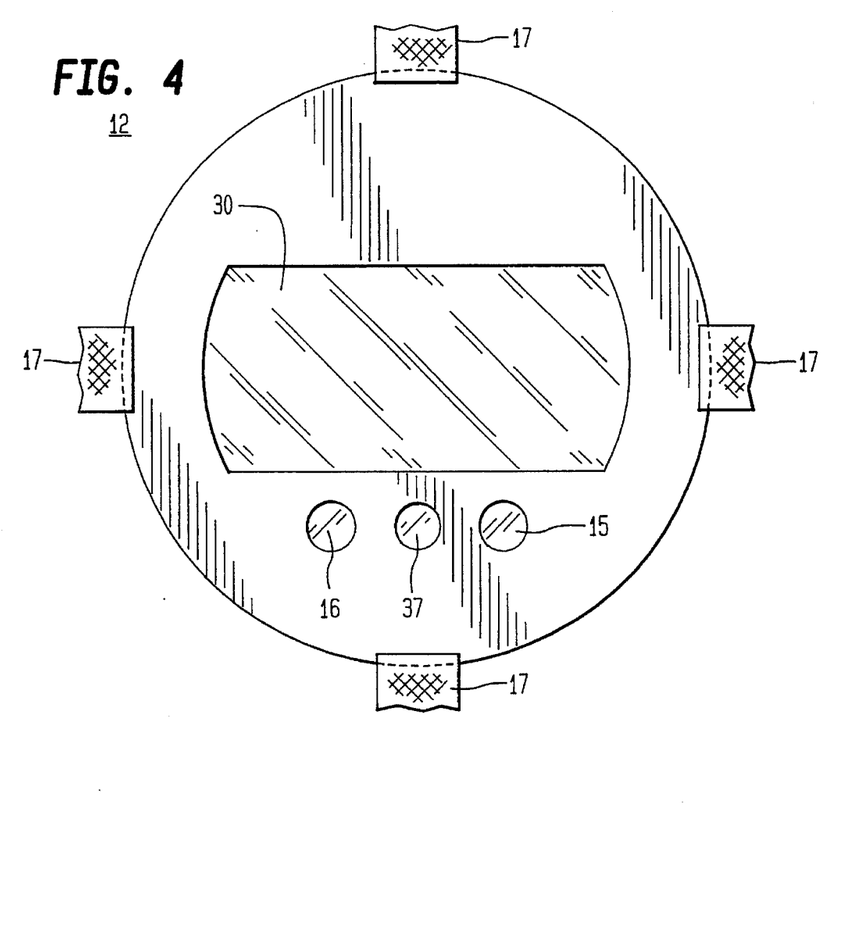
FIG. 4 is a planar view of the outside surface of the lower housing, i.e., the underside of FIG. 1.

Referring to FIG. 1, a plurality of fasteners are secured to the lower housing. It is preferred that the fasteners be velcro or webbed straps 17 that are attached to the lower housing 12, as shown in FIG. 4. The straps 17 attach preferably to at least two locations along the bottom periphery of the lower housing 12 by any means strong enough to support the housing 10 to a target area of a patient.

In the most preferred embodiment shown in FIGS. 1 and 4, the straps 17 are located at four positions around the periphery of the lower housing 12 to secure the housing of the container 10 to the patient. In this embodiment, two straps oppose each other with one of the opposed pair having female means and the other male means in order to secure together the opposed pair of straps. These velcro straps 17 are made of soft nylon webbing sewn to velcro, and they allow for the easy attachment and detachment of housing 10 to and from a target location of a patient. In the most preferred embodiment, the four straps 17 are positioned around the lower housing 12 at 90 degree angles from each other. The apparatus may be secured to the target area of a patient in one of two positions, depending upon which pair of oppositely positioned straps are utilized. It should be understood that more than four straps could be used, however an even number of straps is needed. It should also be understood that any fastening means could be used, however the above is preferred since it provides for readily fastening and unfastening of the container.

Figure 7:
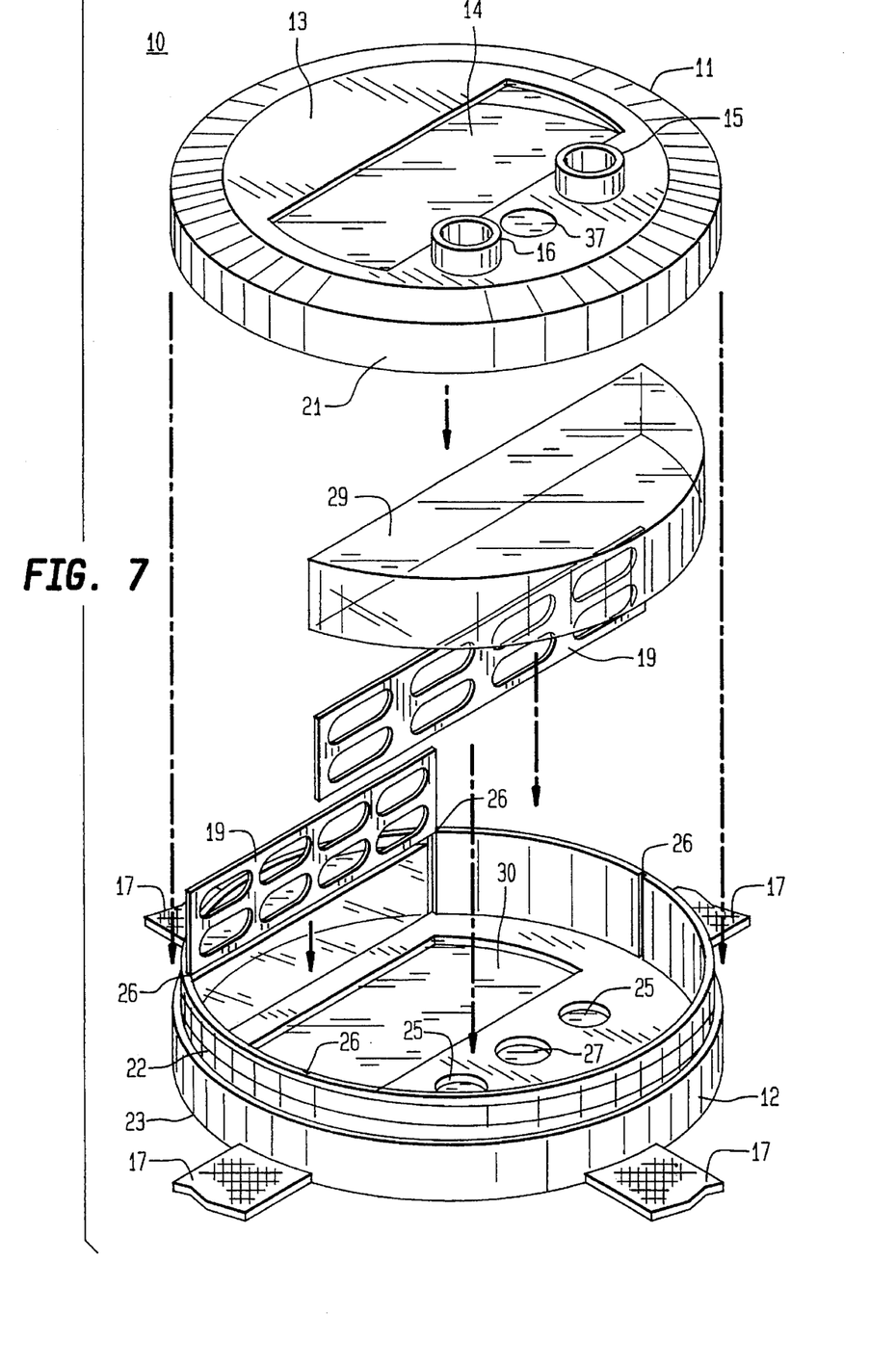
FIG. 7 is an exploded, perspective view that shows the components of the apparatus of FIG. 1.

FIG. 7 illustrates the versatility and flexibility of the container 10. As shown, the upper housing upper housing 11, each fenestrated wall 19, and any formed ice 29 can readily be removed and replaced. The configuration of the preferred embodiment shown in FIG. 7 facilitates the disassembly and cleaning of the present invention, as well as its reassembly. In addition, the configuration may be easily altered by the user to use only one wall 19 and formed ice, or a pair of walls, or no wall at all, depending on the surgery needed or the operator's desire.

Thus, the container or housing 10 provides flexibility for the surgery needed, yet at all times permitting simultaneous cooling of an epidermal region of a patient without obstructing the path of the laser beam. Also, the housing 10 can be readily positioned, and repositioned, on a patient. Further, a laser beam source is directed at a target area, without touching the target area or the patient, and yet without a degradation of the intensity of the laser beam.

The invention having been thus described with particular reference to the preferred forms thereof, it will be obvious that various changes and modifications may be made therein without departing from the spirit and scope of the invention as defined in the appended claims.

Wherefore, I claim:

1. An apparatus adapted to be secured to a patient for treating cutaneous vascular lesions in a target area of the patient, said apparatus comprising:

a lower housing having a bottom with an opening therethrough, an upper housing removably connected in liquid tight engagement to said lower housing, said upper housing having a top with an opening therethrough and substantially in alignment with the opening of said lower housing;

means for connecting said lower housing to said upper housing;

a pair of glass windows, one of said pair of glass windows removably secured in the opening of said lower housing, the other of said pair of glass windows being removably secured in the opening of said upper housing; and at least one fenestrated wall removably positioned at an inner surface of said lower housing to form a first and a second chamber when said upper housing and said lower housing are connected together, said first chamber being adapted to receive a cooling medium, the second chamber for preventing the cooling medium from obstructing a passage of a laser beam between said pair of glass windows, wherein the at least one fenestrated wall permits any portion of the cooling medium that is in liquid form to pass through the apparatus.

2. The apparatus of claim 1, wherein said at least one wall is a pair of walls.

3. The apparatus of claim 1, wherein the at least one fenestrated wall has a plurality of perforations with each perforation of a size to maximize an open area of the perforation and minimize a barrier portion of the at least one fenestrated wall.

4. The apparatus of claim 1, wherein said securing means is a pair of straps, and wherein each pair has a male half and a female half to removably secure said apparatus about a desired portion of a patient.

5. The apparatus of claim 1, wherein said securing means is secured to said lower housing.

6. The apparatus of claim 1, further comprising means adapted for securing said apparatus to the patient.

7. The apparatus of claim 2, wherein said securing means is a strap.

8. The apparatus of claim 1, further comprising means for removing a liquid cooling medium from said apparatus.

9. The apparatus of claim 8, further comprising means for inserting a liquid cooling medium into said apparatus.

10. The apparatus of claim 1, further comprising means for securing the at least one fenestrated wall at the inner surface of said lower housing in said apparatus.

11. The apparatus of claim 10, wherein said securing means are a pair of notches in said lower housing.

12. The apparatus of claim 1, wherein each glass window is made of a quartz glass for optimal transmission of laser energy.

13. The apparatus of claim 12, wherein each glass window is about 0.175 inches in thickness.

14. The apparatus of claim 12, wherein said connecting means is mated threaded surfaces on said lower housing and said upper housing.

15. The apparatus of claim 1, wherein the at least one fenestrated wall has a pair of rows of perforations.

16. The apparatus of claim 15, wherein each row has four perforations.

17. The apparatus of claim 16, wherein each perforation has an elongated oval shape and is about 27 mm by about 6 mm.

18. An apparatus adapted to be secured to a patient for treating cutaneous vascular lesions in a target area of the patient, said apparatus comprising:

a lower housing having a bottom with an opening therethrough, an upper housing removably connected in liquid tight engagement to said lower housing, said upper housing having a top with an opening therethrough and substantially in alignment with the opening of said lower housing, said upper housing having means for removing air and a liquid cooling medium from said apparatus and means for inserting a liquid cooling medium into said apparatus;

means for connecting said lower housing to said upper housing;

a pair of glass windows, one of said pair of glass windows removably secured in the opening of said lower housing, the other of said pair of glass windows being removably secured in the opening of said upper housing;

a pair of fenestrated walls each removably positioned at an inner surface of said lower housing to form a first chamber, a second chamber and a third chamber when said upper housing and said lower housing are connected together, said first and third chambers each being adapted to receive a solid cooling medium, the second chamber for preventing the solid cooling medium from obstructing a passage of a laser beam between said pair of glass windows and for containing a liquid cooling medium; and means adapted for securing said apparatus to the patient, wherein said pair of fenestrated walls permit any portion of the liquid cooling medium to pass through the apparatus.

19. The apparatus of claim 18, wherein said second chamber formed by said pair of fenestrated walls is aligned with said pair of glass windows.

20. The apparatus of claim 18, wherein each of said pair of glass windows is made of a quartz glass for optimal transmission of laser energy.

21. The apparatus of claim 20, wherein each of said pair of fenestrated walls has a plurality of rows of perforations of a size to maximize an open area of each perforation and minimize a barrier portion of the at least one fenestrated wall.

* * * * *